US010779725B2

(12) United States Patent
Su et al.

(10) Patent No.: US 10,779,725 B2
(45) Date of Patent: Sep. 22, 2020

(54) TEAR FILM BREAK-UP TIME MEASUREMENT FOR SCREENING DRY EYE DISEASE BY DEEP CONVOLUTIONAL NEURAL NETWORK

(71) Applicant: YUAN ZE UNIVERSITY, Taoyuan (TW)

(72) Inventors: Tai-Yuan Su, Taoyuan (TW); Zi-Yuan Liu, Taoyuan (TW); Duan-Yu Chen, Taoyuan (TW)

(73) Assignee: Yuan Ze University, Taoyuan (TW)

( * ) Notice: Subject to any disclaimer, the term of this patent is extended or adjusted under 35 U.S.C. 154(b) by 72 days.

(21) Appl. No.: 16/239,847

(22) Filed: Jan. 4, 2019

(65) Prior Publication Data
US 2020/0214554 A1 Jul. 9, 2020

(51) Int. Cl.
| A61B 3/10 | (2006.01) |
| G16H 30/40 | (2018.01) |
| A61B 3/14 | (2006.01) |
| G01N 13/04 | (2006.01) |
| A61B 3/00 | (2006.01) |
| G06T 7/00 | (2017.01) |

(52) U.S. Cl.
CPC ........... *A61B 3/101* (2013.01); *A61B 3/14* (2013.01); *G01N 13/04* (2013.01); *G16H 30/40* (2018.01); *A61B 3/0025* (2013.01); *G06T 7/0012* (2013.01); *G06T 2207/20084* (2013.01); *G06T 2207/30041* (2013.01)

(58) Field of Classification Search
CPC ...................................................... A61B 3/101
USPC ............................................................ 351/206
See application file for complete search history.

(56) References Cited

U.S. PATENT DOCUMENTS

2006/0210122 A1* 9/2006 Cleveland .......... G06K 9/00604
382/117
2017/0357879 A1* 12/2017 Odaibo .................... A61B 3/14

\* cited by examiner

*Primary Examiner* — James C. Jones
(74) *Attorney, Agent, or Firm* — Rosenberg, Klein & Lee

(57) ABSTRACT

A convolutional neural network model distinguishes eyelash images, break-up area images, non-break-up images, sclera images and eyelid images corresponding to a first prediction score, a second prediction score, a third prediction score, a fourth prediction score and a fifth prediction score to respectively produce a first label, a second label, a third label, a fourth label and a fifth label, thereby a break-up area can be detected in a tear film image and a tear film break-up time can be quantized for detection.

7 Claims, 9 Drawing Sheets

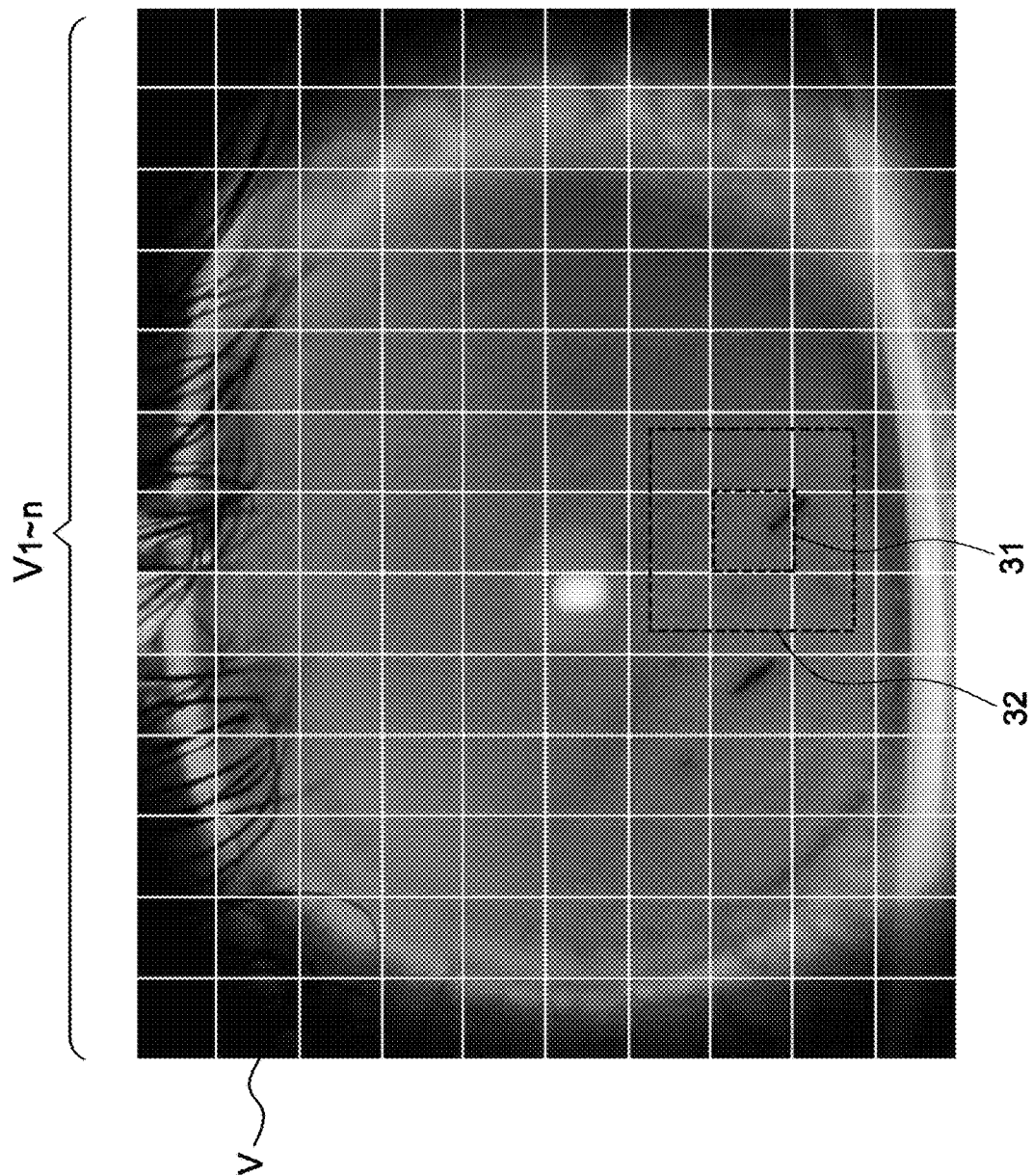

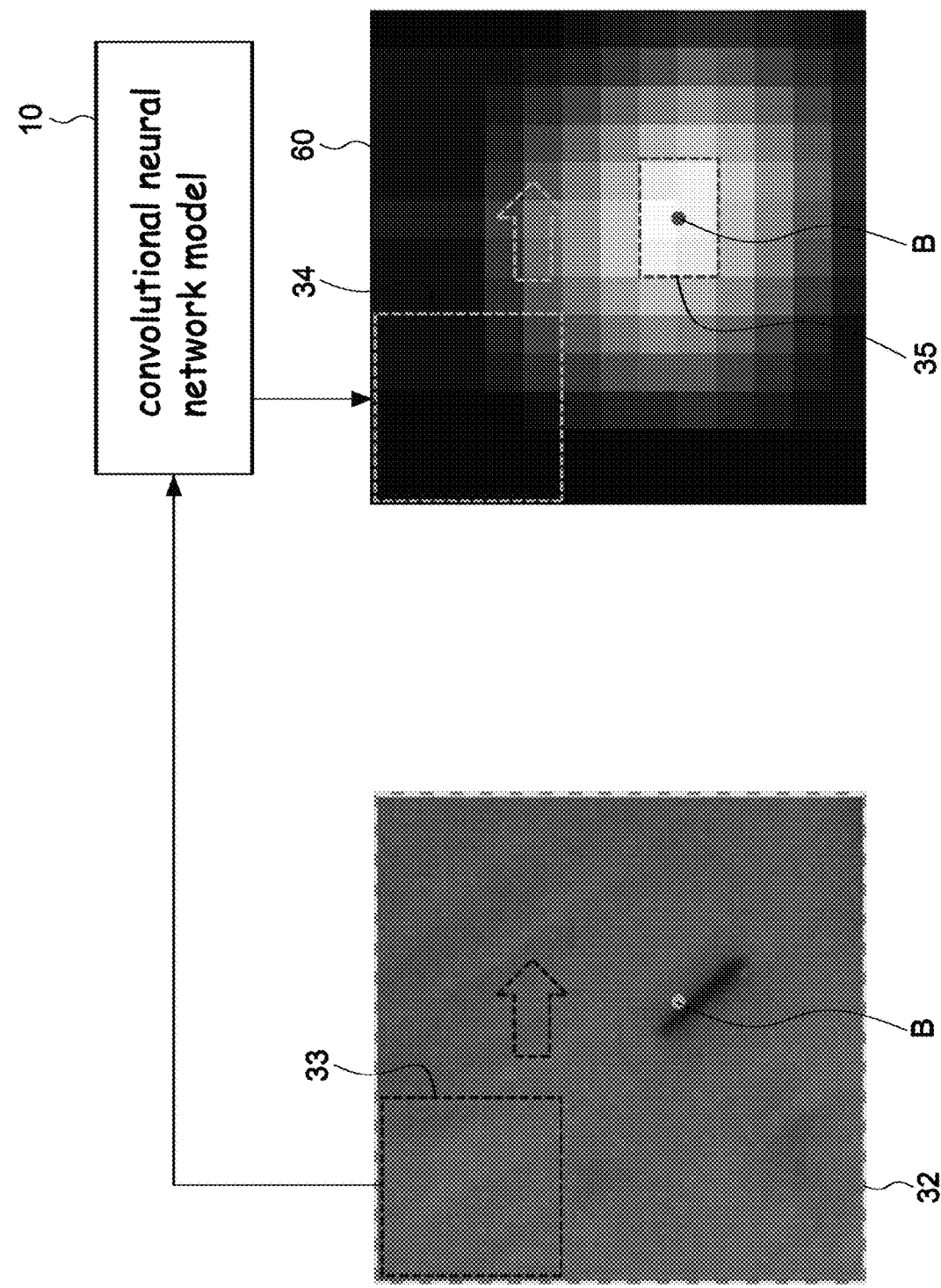

TEAR FILM BREAK-UP TIME MEASUREMENT FOR SCREENING DRY EYE DISEASE BY DEEP CONVOLUTIONAL NEURAL NETWORK

BACKGROUND OF THE INVENTION

1. Field of the Invention

The present invention relates to a method for detection of tear film break-up time to evaluate the stability of tear films objectively and automatically.

2. Description of the Related Art

Dry eye disease is the most common disease in clinical ophthalmology, taking 10-15% of human population. The main reason of dry eye disease is poor quality of tears in the long term, causing inflammation of the eyes. The stability of the tear film is the reason of the poor quality of tears. Traditionally, ophthalmologists would perform the fluorescein dye test to evaluate the condition of patients' eyes. Firstly, applying a drop of fluorescein in one of the eyes and shining a cobalt blue light onto the eye. The green fluorescein dye would be produced for the ophthalmologists to observe and thereby decide the stability of the tear film; the tear film is less stable as time passing by and a break-up area would appear. The ophthalmologists can therefore decide whether the tear film is stable or not; the longer durability before the break-up area appears means the better condition of the tear film Normally the time for deciding whether the tear film is stable or not is 5 seconds; in other words, those has the break-up area appearing less than 5 seconds would be classified to the unstable group. Such method has been commonly applied in clinical practices, but obviously it depends on the observer's—the ophthalmologist's—judgement. On the other hand, such method does not include a quantized standard for the ophthalmologists to follow, making it impossible for reproduction.

SUMMARY OF THE INVENTION

It is a primary objective of the present invention to provide a method for tear film break-up measurement by convolutional neural network. The method analyzes stability of tear film to produce and quantize a time period for distinguishing the stability of the tear film, therefore the method can be applied to dry eye disease detection in clinical analysis.

In order to achieve the objective above, the present invention comprises the following steps: a) providing a convolutional neural network model including a first convolutional layer, a max pooling layer, a second convolutional layer, a first average pooling layer, a third convolutional layer, a second average pooling layer, a fourth convolutional layer, a third average pooling layer, a fifth convolutional layer, a fully connected layer and a softmax layer; b) setting sizes of a first filter, a second filter, a third filter, a fourth filter, a fifth filter and a sixth filter and disposing respectively on said first convolutional layer, said second convolutional layer, said third convolutional layer, said fourth convolutional layer, said fifth convolutional layer and said fully connected layer; c) dividing and selecting a plurality of eyelash images, a plurality of break-up area images, a plurality of non-break-up area images, a plurality of sclera images and a plurality of eyelid images in a tear film image to said first convolutional layer, said max pooling layer, said second convolutional layer, said first average pooling layer, said third convolutional layer, said second average pooling layer, said fourth convolutional layer, said third average pooling layer, said fifth convolutional layer, said fully connected layer and said softmax layer; d) forming said eyelash images, said break-up area images, said non-break-up area images, said sclera images and said eyelid images to produce a first feature map through said first filter, said first feature map being processed by said max pooling layer, and then producing a second feature map through said second filter, said second feature map being processed by said first average pooling layer, then producing a third feature map through said third filter, said third feature map being processed by said second average pooling layer, then producing a fourth feature map through a fourth filter, said fourth feature map being processed by said third average pooling layer to said fully connected layer, so that results of the eyelash images, the break-up area images, the non-break-up area images, the sclera images and the eyelid images are inserted to the fully connected layer; e) classifying said eyelash images, said break-up area images, said non-break-up area images, said sclera images and said eyelid images output from the fully connected layer through said softmax layer, said eyelash images, said break-up area images, said non-break-up area images, said sclera images and said eyelid images respectively corresponding to a first prediction score, a second prediction score, a third prediction score, a fourth prediction score and a fifth prediction score to respectively produce a first label, a second label, a third label, a fourth label and a fifth label; and f) distinguishing said eyelash images, said break-up area images, said non-break-up area images, said sclera images and said eyelid images by said first label, second label, third label, fourth label and said fifth label to detect a tear film break-up area in said tear film image as the image changes with time passing by and to quantize a tear film break-up time.

Further to the measurement method disclosed above, the tear film break-up time is set at 5 seconds and the feature maps are either stable or unstable. The tear film image can be fluorescent, ultraviolet, visible lighting, infrared or thermal.

The first filter has a number of 32, a 5×5 size and a stride of 1, and after max pooling in the max pooling layer, the size of the first filter is altered to 3×3 and the stride is altered to 2. The second filter has a number of 32, a 5×5 size and a stride of 1, and after average pooling in the first average pooling layer, the size of the second filter is altered to 3×3 and the stride is altered to 2. The third filter has a number of 64, a 5×5 size and a stride of 1, and after average pooling in the second average pooling layer, the size of the third filter is altered to 3×3 and the stride is altered to 2. The fourth filter has a number of 64, a size of 5×5 and a stride of 1. The fifth filter has a number of 128, a size of 4×4 and a stride of 1. And the sixth filter has a number of 3, a size of 1×1 and a stride of 1.

In the process mentioned above, the tear film image is divided into a grid as each segment of the grid corresponding to one of the eyelash images, break-up area images, non-break-up area images, sclera images and eyelid images with 96×96 pixels of each segment; a first region of interest retrieved from one of the segments with 96×96 pixels for detecting the break-up area images and then extended to a second region of interest with 260×260 pixels, said second region of interest having a third region of interest with 96×96 pixels and a stride of 20, said third region of interest connected to the convolutional neural network model for segmentation of the second region of interest with 260×260 pixels and output of a probability of said second region of interest being a break-up area image, said probability then added to a probability map, said probability map set selecting a fourth region of interest with an average probability exceeding 0.8 and a center of said fourth region of interest defined as a center of break-up, said fourth region of interest thereby creating a fifth region of interest for detection of the tear film break-up area.

On the other hand, before dividing and selecting the eyelash images, the break-up area images, the non-break-up area images, the sclera images and the eyelid images in the tear film image, the tear film image is detected for eyes opening and closing by a distance between the eyelids in the image.

With the method stated above, the analysis of tear film can be stable and effective, saving time for clinical diagnosis of dry eye disease by providing trustworthy results.

BRIEF DESCRIPTION OF THE DRAWINGS

FIG. 6A is a schematic diagram illustrating a first region of interest thereof extended to a second region of interest thereof according to the present invention;

FIG. 6B is a schematic diagram illustrating a third region of interest thereof divided from the second region of interest according to the present invention;

FIG. 6C is a schematic diagram illustrating a fifth region of interest thereof formed from a fourth region of interest thereof according to the present invention.

DETAILED DESCRIPTION OF THE PREFERRED EMBODIMENT

Figure 1:
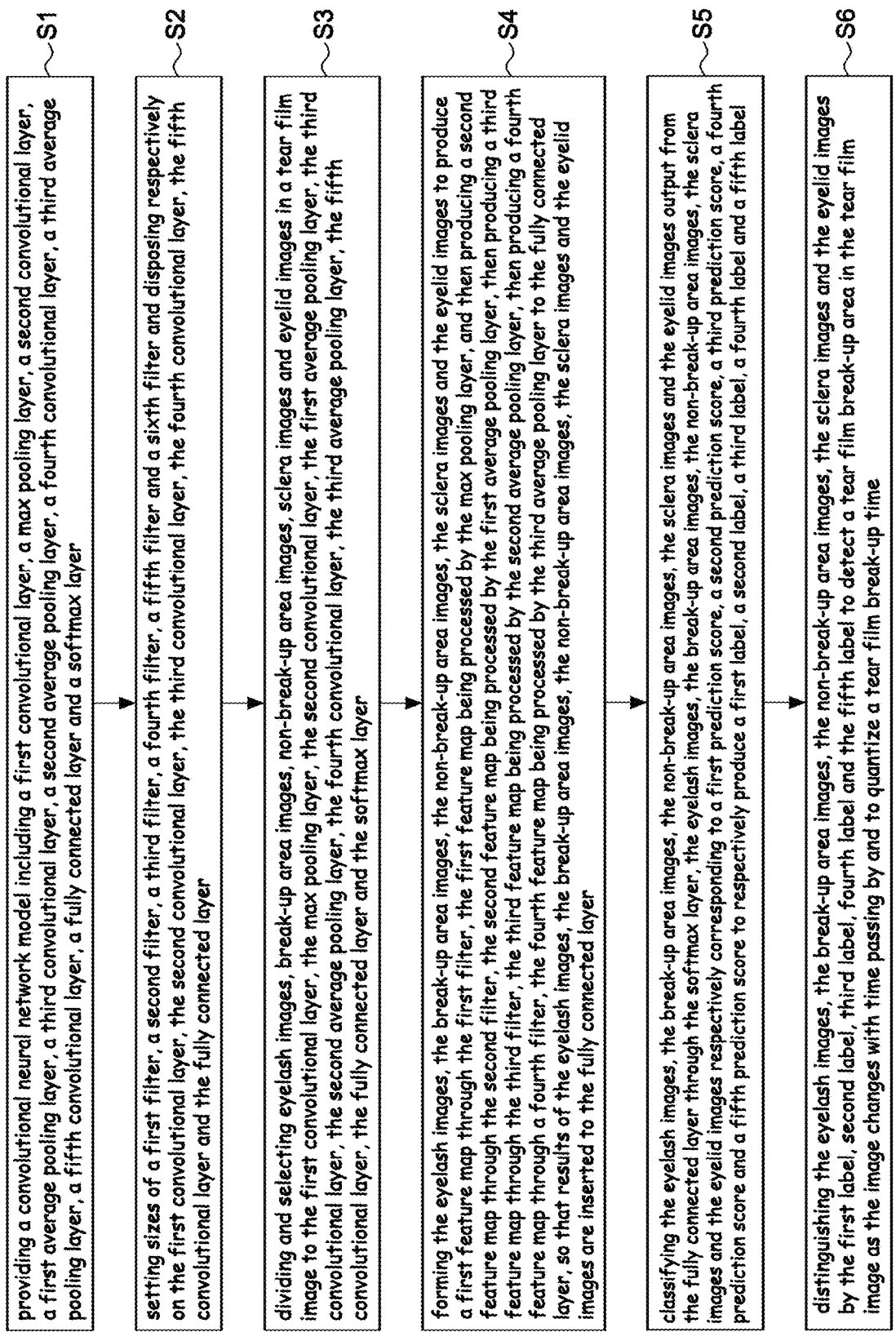
FIG. 1 is a flow diagram of the present invention.

Referring to the flow diagram in FIG. 1 with coordination of FIGS. 2-6D, the present invention includes steps S1-S6 as following.

Step 1 S1: providing a convolutional neural network model 10 including a first convolutional layer 11, a max pooling layer 12, a second convolutional layer 13, a first average pooling layer 14, a third convolutional layer 15, a second average pooling layer 16, a fourth convolutional layer 17, a third average pooling layer 18, a fifth convolutional layer 19, a fully connected layer F and a softmax layer T.

Figure 2:
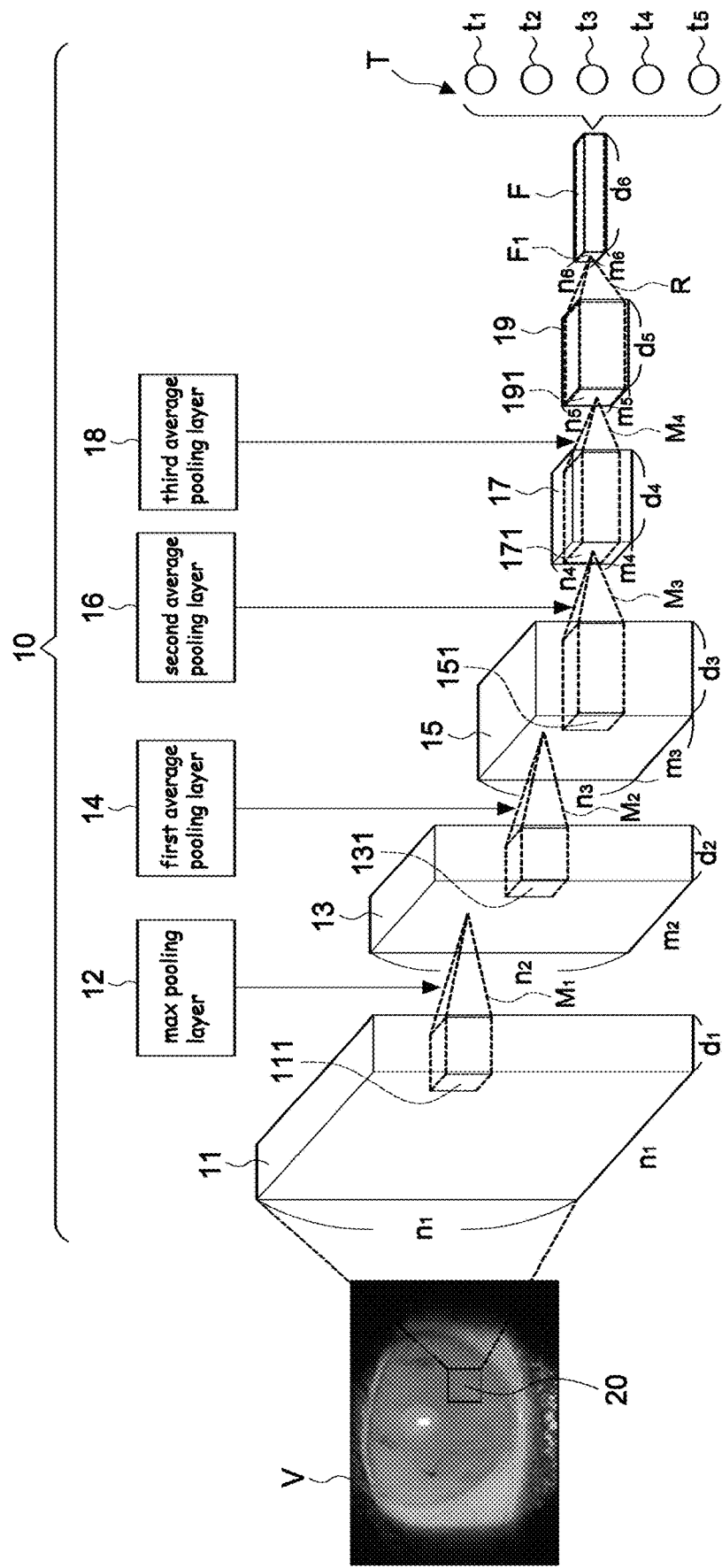
FIG. 2 is a schematic diagram illustrating structure of a convolutional neural network model of the present invention.
Figure 3:
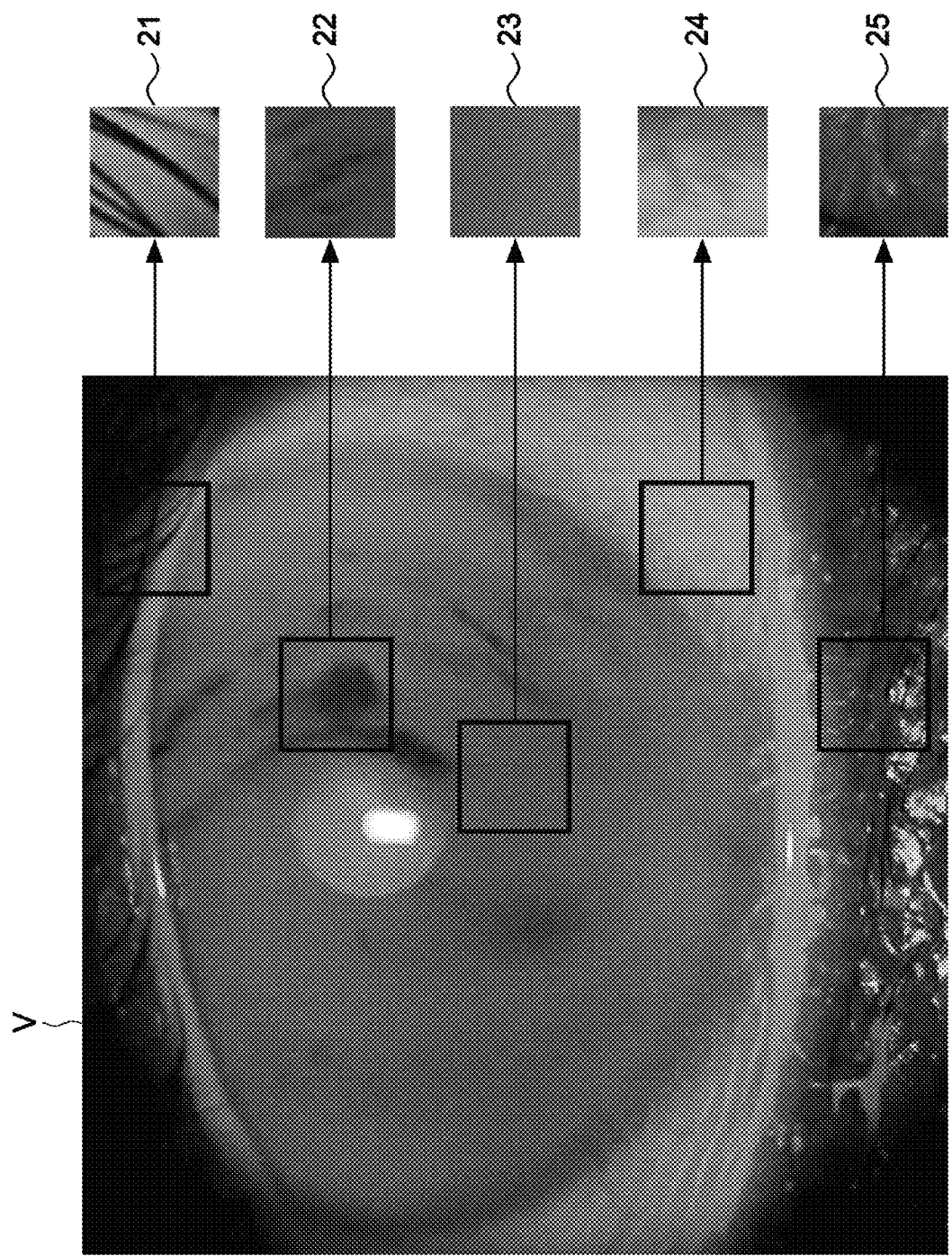
FIG. 3 is a schematic diagram illustrating dividing and selecting partial image according to the present invention.
Figure 4:
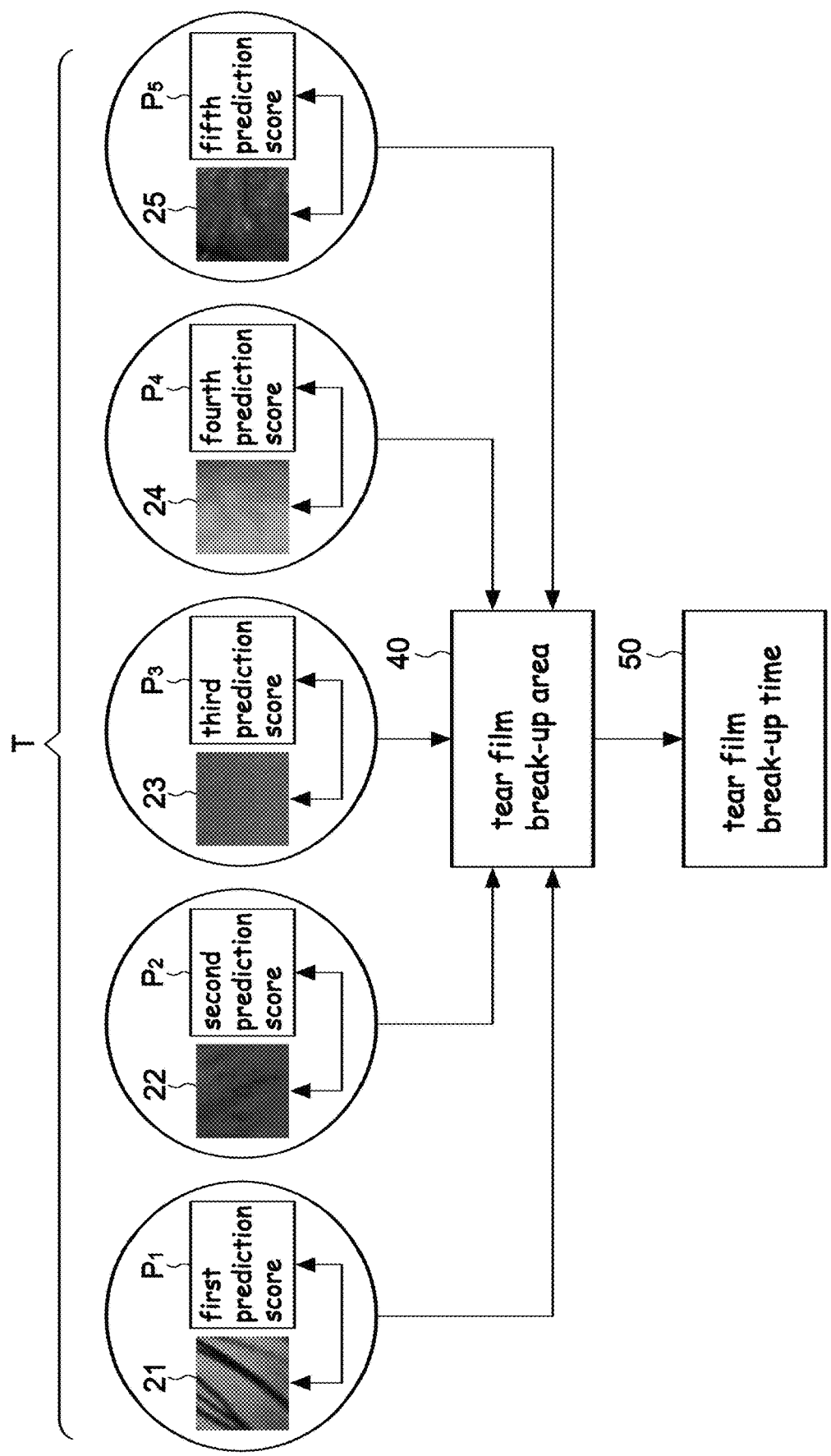
FIG. 4 is a schematic diagram illustrating partial images thereof and corresponding prediction scores forming corresponding labels according to the present invention.

Step 2 S2: setting sizes of a first filter 111, a second filter 131, a third filter 151, a fourth filter 171, a fifth filter 191 and a sixth filter $F_1$; the filters are respectively disposed on the first convolutional layer 11, the second convolutional layer 13, the third convolutional layer 15, the fourth convolutional layer 17, the fifth convolutional layer 19 and the fully connected layer F. Referring to FIG. 2, an output from one of the layers is then input to its neighboring layer so that the network can perform categorizing more precisely, and each depth of the convolutional neural network model 10 is trained individually to capture specific features of the selected image. Furthermore, retrieving a partial image 20 with 96×96×3 pixels output to the first convolutional layer 11. The first filter 111 has a number of 32, a 5×5 size and a stride of 1, outputting the partial image 20 with 96×96×32 pixels $m_1Xn_1Xd_1$; after max pooling in the max pooling layer 12, the size of the first filter 111 is altered to 3×3 and the stride is altered to 2, outputting the partial image 20 with 48×48×32 pixels $m_2Xn_2Xd_2$. Then the partial image 20 with 48×48×32 pixels $m_2Xn_2Xd_2$ is output to the second filter 131 which has a number of 32, a 5×5 size and a stride of 1, further outputting the partial image 20 for average pooling in the first average pooling layer 14; the size of the second filter 131 is altered to 3×3 and the stride is altered to 2, thereby outputting the partial image 20 with 24×24×32 pixels to the third convolutional layer 15. The third filter 151 has a number of 64, a 5×5 size and a stride of 1, outputting the partial image 20 with 24×24×64 pixels $m_3Xn_3Xd_3$; after average pooling in the second average pooling layer 16, the size of the third filter 151 is altered to 3×3 and the stride is altered to 2, outputting the partial image 20 with 12×12×64 pixels. Then the partial image 20 with 48×48×32 pixels is output to the fourth layer 17. The fourth filter 171 has a number of 64, a size of 5×5 and a stride of 1, outputting the partial image 20 with 8×8×64 pixels $m_4Xn_4Xd_4$; after average pooling in the third average pooling layer 18, the partial image 20 is output with 4×4×64 pixels $m_5Xn_5Xd_5$ to the fifth convolutional layer 19. The fifth filter 191 has a number of 128, a size of 4×4 and a stride of 1, outputting the partial image 20 with Ix 1×128 pixels $m_6Xn_6Xd_6$ to the fully connected layer F through the sixth filter $F_1$ which has a number of 3, a size of 1×1 and a stride of 1 and outputs the partial image 20 with 1×1×3 pixels to the softmax layer T, and eventually the partial image 20 is output with 1×1×1 pixels.

Step 3 S3: dividing and selecting a plurality of eyelash images 21, a plurality of break-up area images 22, a plurality of non-break-up area images 23, a plurality of sclera images 24, and a plurality of eyelid images 25 in a tear film image V to the first convolutional layer 11, the max pooling layer 12, the second convolutional layer 13, the first average pooling layer 14, the third convolutional layer 15, the second average pooling layer 16, the fourth convolutional layer 17, the third average pooling layer 18, the fifth convolutional layer 19, the fully connected layer F and the softmax layer T. In this embodiment, the partial image 20 is one of the eyelash images 21, break-up area images 22, non-break-up area images 23, sclera images 24 and the eyelid images 25.

Figure 5B:
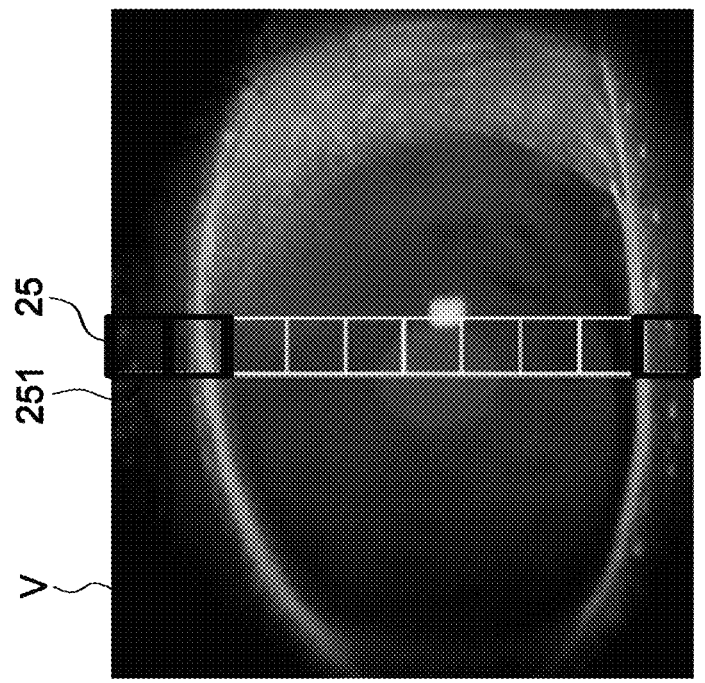
FIG. 5B is a schematic diagram showing the present invention detecting eyes opened.
Figure 5A:
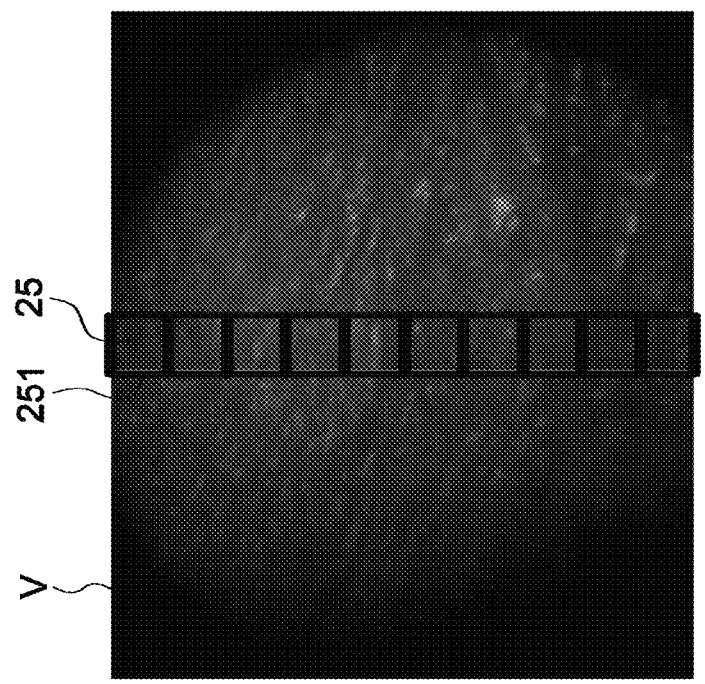
FIG. 5A is a schematic diagram showing the present invention detecting eyes closed.
Figure 5C:
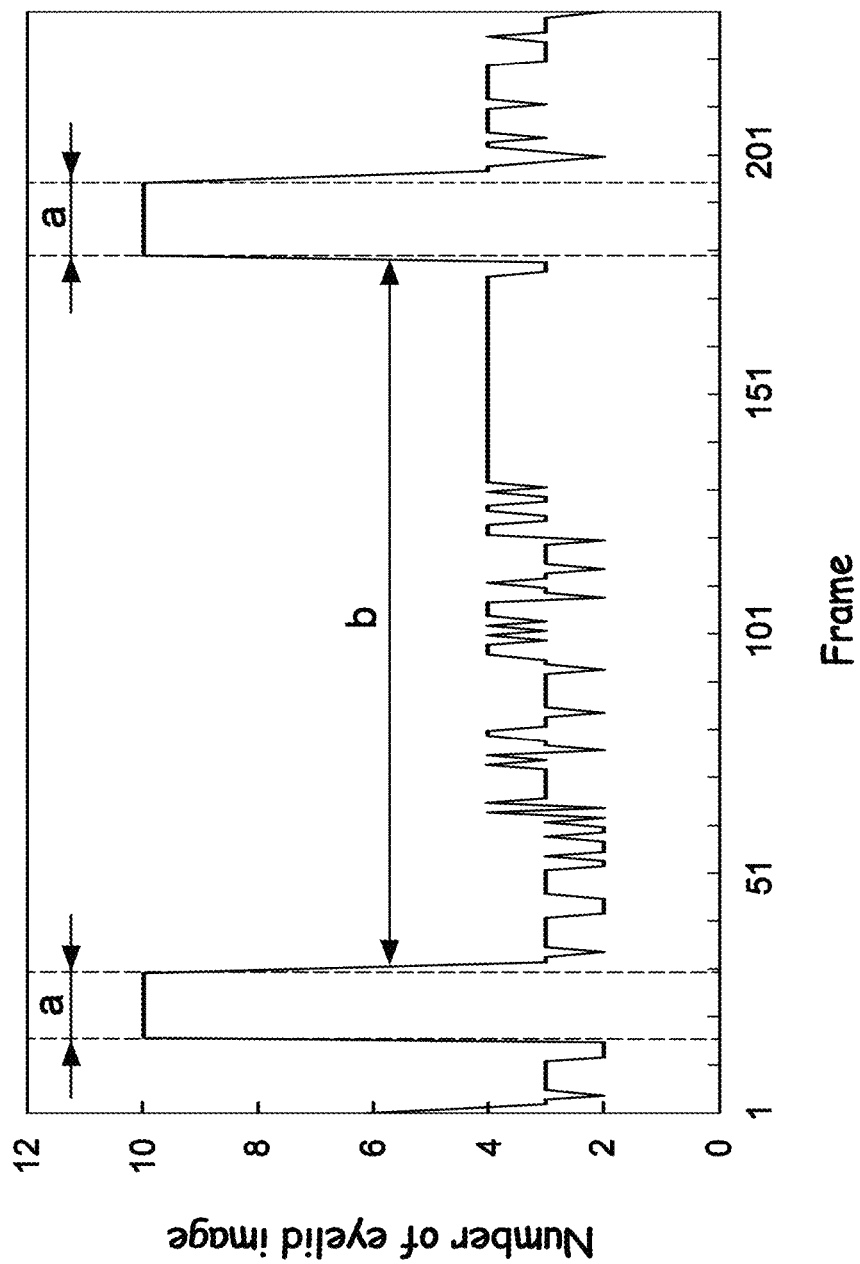
FIG. 5C is a detection result of the present invention detection eyes closed or opened.

Before dividing and selecting the eyelash images 21, the break-up area images 22, the non-break-up area images 23, the sclera images 24 and the eyelid images 25 in the tear film image V, the tear film image V is detected for eyes opening and closing by a distance between the eyelids in the image. In FIG. 5A, ten regions 251 are divided in the tear film image V and detected as the eyelid images 25; therefore it is an image of closed eyes. In FIG. 5B, three of the ten regions 251 are detected as the eyelid images 25; therefore it is an image of opened eyes. Further referring to FIG. 5C, the present invention detects a number of the eyelid images 25 and thereby learns a first duration a in the frame is the duration of eyes closed and a second duration b in the frame is the duration of eyes opened. But the present invention is not limited to such application.

Step 4 S4: forming the eyelash images 21 the break-up area images 22, the non-break-up area images 23, the sclera images 24 and the eyelid images 25 to produce a first feature map $M_1$ through the first filter 111. The first feature map $M_1$ is then processed by the max pooling layer 12, producing a second feature map $M_2$ through the second filter 131. The second feature map $M_2$ is processed by the first average pooling layer 14, producing a third feature map $M_3$ through the third filter 151. The third feature map $M_3$ is processed by the second average pooling layer 16, producing a fourth feature map 171 through a fourth filter 171 The fourth feature map $M_4$ is processed by the third average pooling layer 17 to the fully connected layer F, so that the results of the eyelash images 21, the break-up area images 22, the non-break-up area images 23, the sclera images 24 and the eyelid images 25 are inserted to the fully connected layer F. In short, the features can capture the discriminatory information of the image through convolution. In this embodiment, the feature maps are either stable or unstable and the tear film image V is fluorescent, ultraviolet, visible lighting, infrared or thermal. But the present invention is not limited to such application.

Step 5 S5: classifying the eyelash images 21, the break-up area images 22, the non-break-up area images 23, the sclera images 24 and the eyelid images 25 output from the fully connected layer F through the softmax layer T. The eyelash images 21, the break-up area images 22, the non-break-up area images 23, the sclera images 24 and the eyelid images 25 respectively corresponds to a first prediction score $P_1$, a second prediction score $P_2$, a third prediction score $P_3$, a fourth prediction score $P_4$ and a fifth prediction score $P_5$ to respectively produce a first label $t_1$, a second label $t_2$, a third label $t_3$, a fourth label $t_4$ and a fifth label $t_5$.

Step 6 S6: distinguishing the eyelash images 21, the break-up area images 22, the non-break-up area images 23, the sclera images 24 and the eyelid images 25 by the first label $t_1$, the second label $t_2$, the third label $t_3$, the fourth label $t_4$ and the fifth label $t_5$ to detect a tear film break-up area 40 in the tear film image V as the image changes with time passing by and to quantize a tear film break-up time 50. In this embodiment, the tear film break-up time 50 is set at 5 seconds. Therefore, if a fluorescent tear film break-up time is equal to or less than 5 seconds, it is classified to a dry eye group, and if the break-up time is more than 5 seconds, it is classified to a normal group. But the present invention is not limited to such application.

Figure 6D:
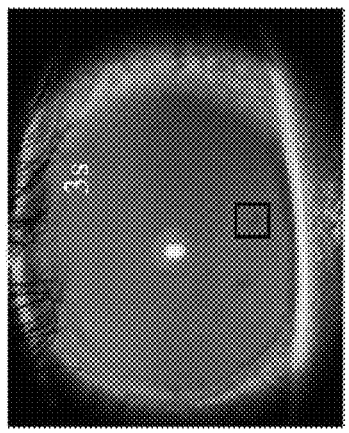
FIG. 6D is a series of schematic diagrams illustrating the time period during a tear film break-up according to the present invention.
Figure 6D:
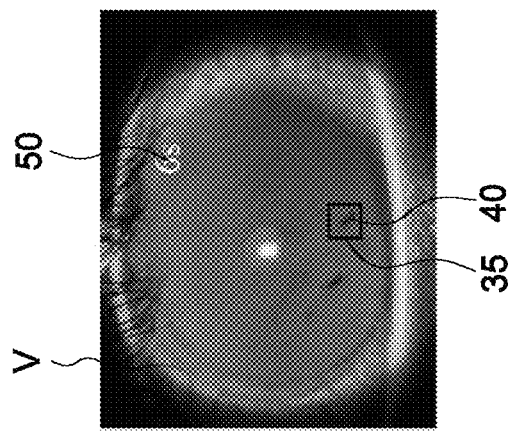
Figure 6D:
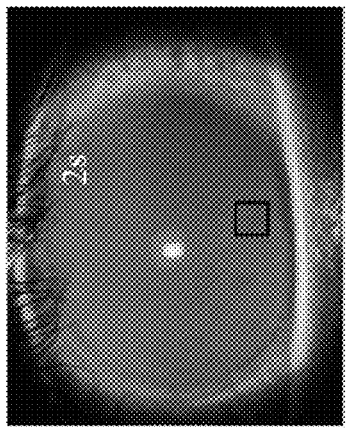
Figure 6D:
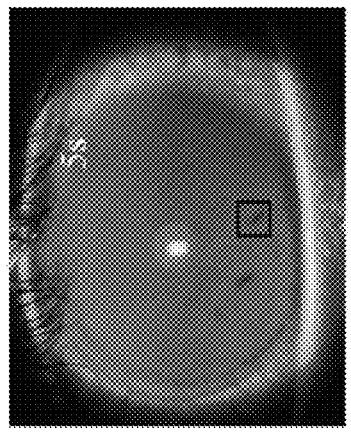
Figure 6D:
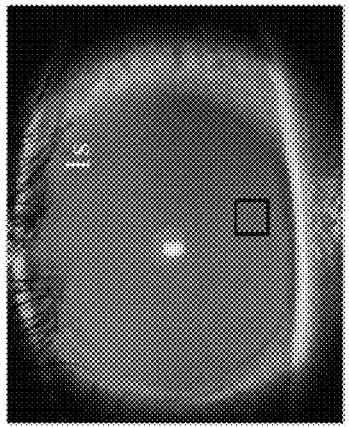
Figure 6D:
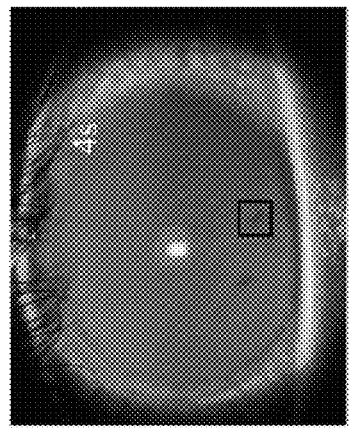

With reference to FIG. 6A, the tear film image V is divided into a grid $V_{1-n}$ as each segment of the grid $V_{1-n}$ is corresponding to one of the eyelash images 21, break-up area images 22, non-break-up area images 23, sclera images 24 and eyelid images 25 with 96×96 pixels of each segment. A first region of interest 31 is retrieved from one of the segments with 96×96 pixels for detecting the break-up area images 21 and then extended to a second region of interest 32 with 260×260 pixels. With reference to FIG. 6B, the second region of interest 32 has a third region of interest 33 with 96×96 pixels and a stride of 20; the third region of interest 33 is connected to the convolutional neural network model 10 for segmentation of the second region of interest 32 with 260×260 pixels and output of a probability of the second region of interest 32 being a break-up area image 21. With reference to FIG. 6C, the probability is then added to a probability map 60 which is set selecting a fourth region of interest 34 with an average probability exceeding 0.8 and a center of the fourth region of interest 34 is defined as a center of break-up B, thereby the fourth region of interest 34 is able to create a fifth region of interest 35 for detection of the tear film break-up area 40. When the break-up area image 21 is detected, the tear film break-up time 50 can be obtained. As shown in FIG. 6D, images of the tear film image V from 1 second to 6 seconds are retrieved and, after training, whether the tear film break-up area 40 appears in the images can be detected. According to the images, the tear film break-up area 40 appears at 5 seconds; therefore, the tear film break-up time 50 is 5 seconds.

The tear film break-up time 50 is a stable indication of clinical diagnosis of eyes which represents the time period needed until the break-up appears after a blink. In this embodiment, the convolutional neural network model 10 is applied to detecting the tear film break-up time 50 after a training process of six layers of the model. Consequently, the present invention is able to detect and decide the stability of tear films objectively and conveniently as an auxiliary tool to ophthalmologists in clinical practices.

Although particular embodiment of the invention has been described in detail for purposes of illustration, various modifications and enhancements may be made without departing from the spirit and scope of the invention. Accordingly, the invention is not to be limited except as by the appended claims.

What is claimed is:

1. A tear film break-up time measurement method for screening dry eye disease by deep convolutional neural network, comprising steps as following:

providing a convolutional neural network model including a first convolutional layer, a max pooling layer, a second convolutional layer, a first average pooling layer, a third convolutional layer, a second average pooling layer, a fourth convolutional layer, a third average pooling layer, a fifth convolutional layer, a fully connected layer and a softmax layer;

setting sizes of a first filter, a second filter, a third filter, a fourth filter, a fifth filter and a sixth filter and disposing respectively on said first convolutional layer, said second convolutional layer, said third convolutional layer, said fourth convolutional layer, said fifth convolutional layer and said fully connected layer;

dividing and selecting a plurality of eyelash images, a plurality of break-up area images, a plurality of non-break-up area images, a plurality of sclera images and a plurality of eyelid images in a tear film image to said first convolutional layer, said max pooling layer, said second convolutional layer, said first average pooling layer, said third convolutional layer, said second average pooling layer, said fourth convolutional layer, said third average pooling layer, said fifth convolutional layer, said fully connected layer and said softmax layer;

forming said eyelash images, said break-up area images, said non-break-up area images, said sclera images and said eyelid images to produce a first feature map through said first filter, said first feature map being processed by said max pooling layer, and then producing a second feature map through said second filter, said second feature map being processed by said first average pooling layer, then producing a third feature map through said third filter, said third feature map being processed by said second average pooling layer, then producing a fourth feature map through a fourth filter, said fourth feature map being processed by said third average pooling layer to said fully connected layer, so that results of the eyelash images, the break-up area images, the non-break-up area images, the sclera images and the eyelid images are inserted to the fully connected layer;

classifying said eyelash images, said break-up area images, said non-break-up area images, said sclera images and said eyelid images output from the fully connected layer through said softmax layer, said eyelash images, said break-up area images, said non-break-up area images, said sclera images and said eyelid images respectively corresponding to a first prediction score, a second prediction score, a third prediction score, a fourth prediction score and a fifth prediction score to respectively produce a first label, a second label, a third label, a fourth label and a fifth label; and distinguishing said eyelash images, said break-up area images, said non-break-up area images, said sclera images and said eyelid images by said first label, second label, third label, fourth label and said fifth label to detect a tear film break-up area in said tear film image as the image changes with time passing by and to quantize a tear film break-up time.

2. The tear film break-up time measurement method as claimed in claim 1, wherein the tear film break-up time is set at 5 seconds.

3. The tear film break-up time measurement method as claimed in claim 2, wherein the feature maps are either stable or unstable.

4. The tear film break-up time measurement method as claimed in claim 1, wherein the tear film image is fluorescent, ultraviolet, visible lighting, infrared or thermal.

5. The tear film break-up time measurement method as claimed in claim 1, wherein the first filter has a number of 32, a 5×5 size and a stride of 1, and after max pooling in the max pooling layer, the size of the first filter is altered to 3×3 and the stride is altered to 2; the second filter has a number of 32, a 5×5 size and a stride of 1, and after average pooling in the first average pooling layer, the size of the second filter is altered to 3×3 and the stride is altered to 2; the third filter has a number of 64, a 5×5 size and a stride of 1, and after average pooling in the second average pooling layer, the size of the third filter is altered to 3×3 and the stride is altered to 2; the fourth filter has a number of 64, a size of 5×5 and a stride of 1; the fifth filter has a number of 128, a size of 4×4 and a stride of 1; and the sixth filter has a number of 3, a size of 1×1 and a stride of 1.

6. The tear film break-up time measurement method as claimed in claim 5, wherein the tear film image is divided into a grid as each segment of the grid corresponding to one of the eyelash images, break-up area images, non-break-up area images, sclera images and eyelid images with 96×96 pixels of each segment; a first region of interest retrieved from one of the segments with 96×96 pixels for detecting the break-up area images and then extended to a second region of interest with 260×260 pixels, said second region of interest having a third region of interest with 96×96 pixels and a stride of 20, said third region of interest connected to the convolutional neural network model for segmentation of the second region of interest with 260×260 pixels and output of a probability of said second region of interest being a break-up area image, said probability then added to a probability map, said probability map set selecting a fourth region of interest with an average probability exceeding 0.8 and a center of said fourth region of interest defined as a center of break-up, said fourth region of interest thereby creating a fifth region of interest for detection of the tear film break-up area.

7. The tear film break-up time measurement method as claimed in claim 1, wherein the tear film image is detected for eyes opening and closing by a distance between the eyelids in the image before dividing and selecting the eyelash images, the break-up area images, the non-break-up area images, the sclera images and the eyelid images in the tear film image.

* * * * *